United States Patent [19]

Parsons et al.

[11] 4,369,496

[45] Jan. 18, 1983

[54] APPARATUS FOR HIGH-SPEED TRANSCRIPTION OF RECORDED PHYSIOLOGICAL DATA

[75] Inventors: William R. Parsons, Santa Ana; Christopher T. Bible, El Toro; Donald P. Kannenberg, Garden Grove, all of Calif.

[73] Assignee: Advancemed, Irvine, Calif.

[21] Appl. No.: 128,181

[22] Filed: Mar. 7, 1980

[51] Int. Cl.³ .................. A61B 5/04; G06K 15/02
[52] U.S. Cl. .................. 364/417; 128/731; 346/33 ME; 360/6
[58] Field of Search .............. 364/415–417; 128/711, 731; 346/33 ME; 360/6

[56] References Cited

U.S. PATENT DOCUMENTS

| | | | |
|---|---|---|---|
| 3,874,370 | 4/1975 | Harris et al. | 128/711 |
| 4,006,737 | 2/1977 | Cherry | 128/711 |
| 4,094,310 | 6/1978 | McEachern et al. | 346/33 ME |
| 4,109,243 | 8/1978 | Day et al. | 346/33 ME |
| 4,122,498 | 10/1978 | Dyer | 360/6 |
| 4,173,971 | 11/1979 | Karz | 128/711 X |
| 4,202,354 | 5/1980 | Smith et al. | 128/731 |
| 4,211,238 | 7/1980 | Shu et al. | 346/33 ME |
| 4,212,530 | 7/1980 | Pitts, Jr. | 346/160 |
| 4,215,697 | 8/1980 | Demetrescu | 128/731 |

OTHER PUBLICATIONS

Ives et al.: 4 Channel 24 Hour Cassette Recorder for Long Term EEC Monitoring, Electroencephalography and Clinical Neurophysiology, No. 1, vol. 39, Jul. 1975.
Kinnon: A Miniature 4 Channel Cassette Recorder for Physiological and Other Variables. Biometry II, 2nd Int. Symposium, 1974, pp. 67–70.
Kalocay: Automatic Time Code Recording on Paper, Biomedizinische Technik, vol. 21, No. 5, pp. 140–143, Jun. 1976.
Fine et al.: Processing and Stereophonic Presentation of Physiological Signals, IEEE, Trans. in Bio-Medical Eng., vol. BME-18, No. 1, Jan. 1971, pp. 9–15.

*Primary Examiner*—Felix D. Gruber
*Attorney, Agent, or Firm*—Kendrick, Netter & Bennett

[57] ABSTRACT

A device for high-speed transcription of physiological data recorded at substantially lower speeds includes a device for converting the recorded data into electrical signals, a device for converting the electrical signals into light signals and displaying them with high clarity and resolution, and a device for transcribing the light signals onto light-sensitive media at high speed.

10 Claims, 5 Drawing Figures

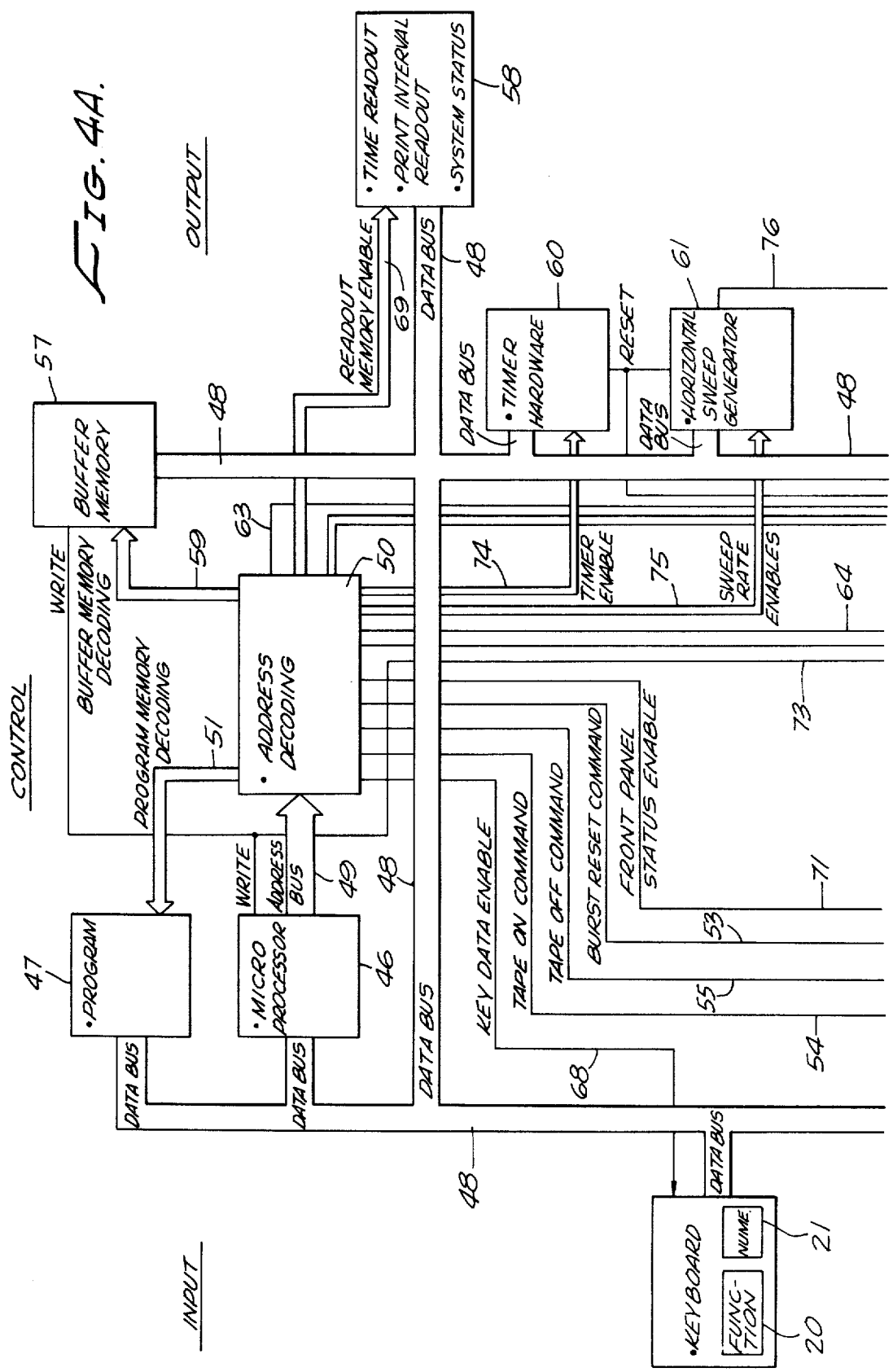

APPARATUS FOR HIGH-SPEED TRANSCRIPTION OF RECORDED PHYSIOLOGICAL DATA

This invention relates to apparatus and methods for high-speed transcription of physiological data recorded at substantially lower speeds. In particular, the invention relates to apparatus and methods for transcribing all or selected portions of such data as ECG and EEG data on light-sensitive media such as photosensitive paper at speeds of 100 to 1,000 or more times faster than the normal recording speed, with a high degree of clarity and resolution.

Modern day medical techniques for detection, treatment and prevention of heart disease require monitoring, recording and transcribing patient ECG data over extended periods of time, and examination of that data for diagnosis and treatment in the shortest possible time. To record the data, electrodes are placed on a patient's torso in one, two or more locations. The resulting electrical ECG signals are recorded on magnetic tape of the reel-to-reel type or of the cassette type over an extended period of time, say 24 hours. During recording, the patient may engage in such normal daily activities as eating, working, exercising and sleeping.

After recording, the data is scrutinized to determine whether the patient's heart exhibits any activity symptomatic of injury or disease. State-of-the-art playback devices for scrutinizing such taped data include high speed tape transports, oscilloscopes for viewing recorded data, chart recorders for printing small portions of that data, and detection circuits for counting abnormal and normal heartbeats. A highly-trained, skilled technician can scrutinize 24 hours of tape-recorded ECG data in 40 to 80 minutes when working efficiently with prior art processors.

Such processors are costly to make and to operate, requiring highly-trained technicians to operate them. Their circuits for counting abnormal and normal heartbeats are often inaccurate. Moreover, because they can print only limited amounts of recorded data, a physician's diagnosis may be and frequently is wrong because he does not see representative data. The physician must rely on the technician's ability to identify abnormal data as the recorded data passes rapidly over an oscilloscope screen, and failure to spot abnormal data is common with such processors.

Accordingly, a need exists for a processor which can transcribe all the physiological data recorded at a first speed, say real time speed, onto tangible media in compact, easy to analyze form, at much higher speeds. Desirably, such a processor would also reference the recorded data to the time at which the data was recorded. A need also exists for a processor which can reproduce selected portions of recorded data in enlarged form for closer scrutiny of data that may indicate disease or damage and require treatment. A need also exists for a processor which is easy to operate, but reliably reproduces all or selected portions of the recorded data, as a physician may require, to diagnose disease or injury based on representative, meaningful recorded data.

This invention provides an apparatus for high-speed transcription of physiological data recorded at speeds substantially lower than the speed of transcription. In particular, this apparatus can transcribe data at rates 100 to 1,000 times faster than the real time recording speeds common to the monitoring of physiological data. The apparatus includes means for converting the recorded physiological data into electrical signals representative thereof, means for high-speed display of those electrical signals as light signals of good clarity and resolution, and means for high-speed transcription of the light signals so obtained onto light-sensitive media.

The means for converting the recorded physiological data into electrical signals representative thereof can be a reel-to-reel tape playback unit or a cassette playback unit of the kind used with magnetic tape. The new apparatus permits converting the recorded data into electrical signals at one or more than one conversion speed. For instance, the speed of conversion can be 1,000 or more times faster than the speed of recording. Moreover, where the recorded physiological data appears on two or more channels of the multichannel magnetic tape, the new processor permits converting data from one channel alone, or from two or more channels simultaneously. Simultaneous transcription from two or more channels permits easy identification of differences between data recorded on the different channels because the data from the several channels can be juxtaposed to one another in transcription.

Among the kinds of recorded physiological data for which the new apparatus is well-suited are electrocardiograph (ECG) signals and electroencephalograph (EEG) signals. However, the processor can also be used for reviewing other kinds of data recorded at real time speeds, but requiring analysis at far higher speeds. Such data include but are not limited to respiratory data, blood pressure, movement of limbs, eye pressure and other symptoms associated with the eye.

In the preferred embodiment, the means for high-speed display of electrical signals as light signals of high clarity and resolution is a fiber-optic recorder means.

The means for high-speed transcription of the light signals includes not only the device which converts electrical signals into light signals, but also includes such light-sensitive media as photosensitive paper. An important advantage of the transcription capability of this new device is that the physician or other user of the transcribed data will have all of the recorded data in relatively permanent form. Typically, the data can appear on one or two sheets of tangible media such as photosensitive paper, and can be made part of a patient's permanent records. This advantage alone makes the new apparatus far better than processors now in use.

The new apparatus can include means for selecting and controlling the quantity of recorded data displayed and transcribed per line on the light-sensitive media. In specific embodiments, using the fiber-optic recorder means for converting electrical signals to light signals, the apparatus can transcribe 30 seconds of data on a line, 60 seconds of data on a line, or as little as 5 or 10 seconds of data on a line. The apparatus can also include means for controlling the size of the transcribed data, which permits enlarging selected portions of the data for closer scrutiny. Thus, the new apparatus permits both transcription of all recorded data, so that the user need not worry that transcribed data is non-representative, and transcription, in enlarged or unenlarged form, of just selected portions of data which hold particular interest.

The new apparatus also provides, in preferred embodiments, for transcribing such alpha-numeric data as the time of recording in conjunction with the recorded data itself. To that end, the apparatus includes display means and means for switching from display of recorded physiological data to display of alpha-numeric data, means for generating horizontal sweeps of the display means for both physiological data and the alpha-numeric data, and means for blanking the display of such data on the display means. Preferred embodiments also include means for entering or selecting the alpha-numeric data for transcription with the physiological data, means for selecting the frequency at which the alpha-numeric data is displayed and transcribed onto light-sensitive media, means for visibly displaying and verifying the alpha-numeric data as it is input, and means for testing the reasonableness of the alpha-numeric data within certain limits.

Preferred embodiments also include means for detecting a recorded signal representing a predetermined point in the recorded physiological data, and means for performing such functions as interrupting, slowing or speeding data conversion upon detection of that signal. Such a signal could represent the beginning of the recorded data, or some other point of interest in the data, such as when a patient whose ECG is being recorded feels an unusual sensation.

Preferred embodiments also include means for automatic high-speed transcription, with or without enlargement, of at least one selected time period of recorded physiological data. Such embodiments permit inputting or selecting several different time periods of data for automatic transcription one after the other, and permit transcribing from one channel of data alone, two channels simultaneously, or more than two channels simultaneously.

This invention can better be understood by reference to the drawings in which:

FIGS. 4A and 4B are a function block diagram of that preferred embodiment.

Figure 1:
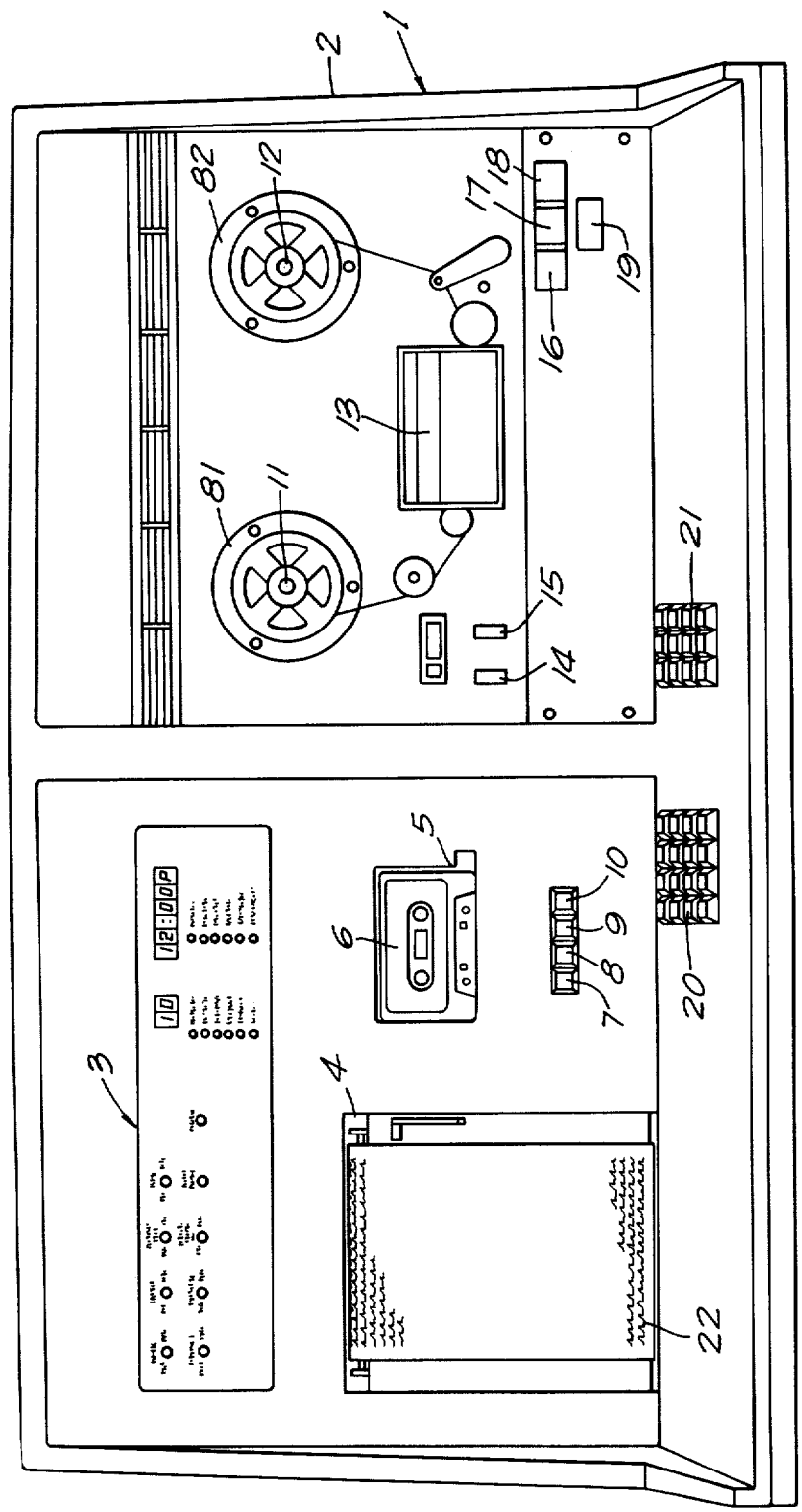
FIG. 1 is an elevation view of the preferred embodiment.

In FIG. 1, processor 1 includes housing 2, control and indicator panel 3, paper-feeding means 4, cassette tape deck holder 5 with cassette tape 6 therein, cassette tape controls 7, 8, 9 and 10, reel-to-reel type playback means 13, control means 14–19 therein, and keyboards 20 and 21 for input of function commands and alpha-numeric data, respectively.

Unlike state-of-the-art processors, processor 1 can transcribe data recorded on cassette tape such as tape deck 6 and/or on reel-to-reel tapes such as reels 23 and 24 shown mounted on spindles 11 and 12, respectively. Controls 7 and 16 rewind the tapes; controls 8 and 17 advance the tapes. Controls 9 and 18 advance the tapes at fast speed; controls 10 and 19 stop tape movement. Control 14 turns power off and on to the main unit. Control 15 changes tape playback speeds, say from 240 times real (recording) time to 480 times real (recording) time.

The new processor delivers the data on tangible media such as photosensitive paper 22 from fiber-optic recorder-printer means generally designated 4.

Figure 2:
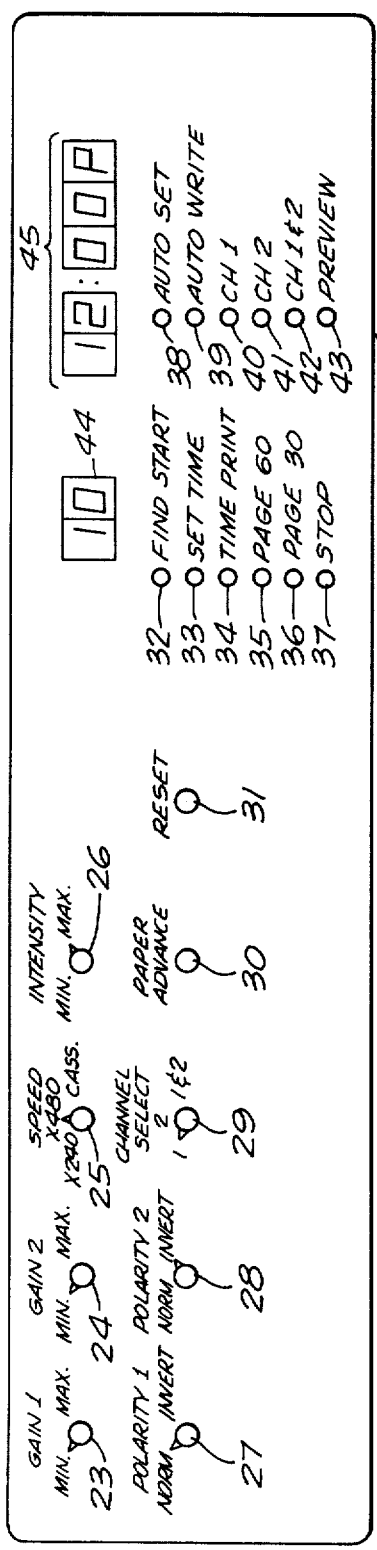
FIG. 2 is an enlarged elevation view of the face plate from that preferred embodiment, showing some of the controls for the device.

Control and indicator panel 3, better seen in FIG. 2, includes nine control means 23–31, twelve indicator lights 32–43, and alpha-numeric displays 44 and 45. Control means 23 and 24 permit selection of maximum or minimum gain for playback (or conversion) of data from channel 1 or channel 2 of two-channel magnetic tape commonly utilized to record ECG data. Control means 27 and 28 permit selection of normal or inverted display and transcription of data waveforms from channels 1 and 2, respectively, of such two-channel tape. Control means 29 permits selection for transcription of data from channel 1, channel 2, or channels 1 and 2 simultaneously. Transcription from channels 1 and 2 simultaneously produces waveforms juxtaposed beside one another, one waveform from the channel 1 data, the other from the channel 2 data.

Indicator light 40 glows when the processor is transcribing only from channel 1. Indicator light 41 glows when the processor is transcribing only from channel 2. Indicator light 42 glows when the processor is transcribing from channels 1 and 2 simultaneously. The other indicator lighs 32–39 and 43 glow when the corresponding key from function keypad 20 is activated.

Control means 25 sets the tape playback speed; control means 26, the intensity of displayed data. (Intensity control signals pass to recorder 66 via path 70. See FIG. 4B.) Control means 31 resets the processor to the normal starting condition. Controls means 30 causes the movement of photosensitive paper past the face plate of the fiber-optic recorder means. Alpha-numeric display 44 shows the frequency with which alpha-numeric data is transcribed on the photosensitive paper. Alpha-numeric display 45, when properly set, shows the actual time that data passing the face plate of the fiber-optic recorder means was recorded.

Figure 3:
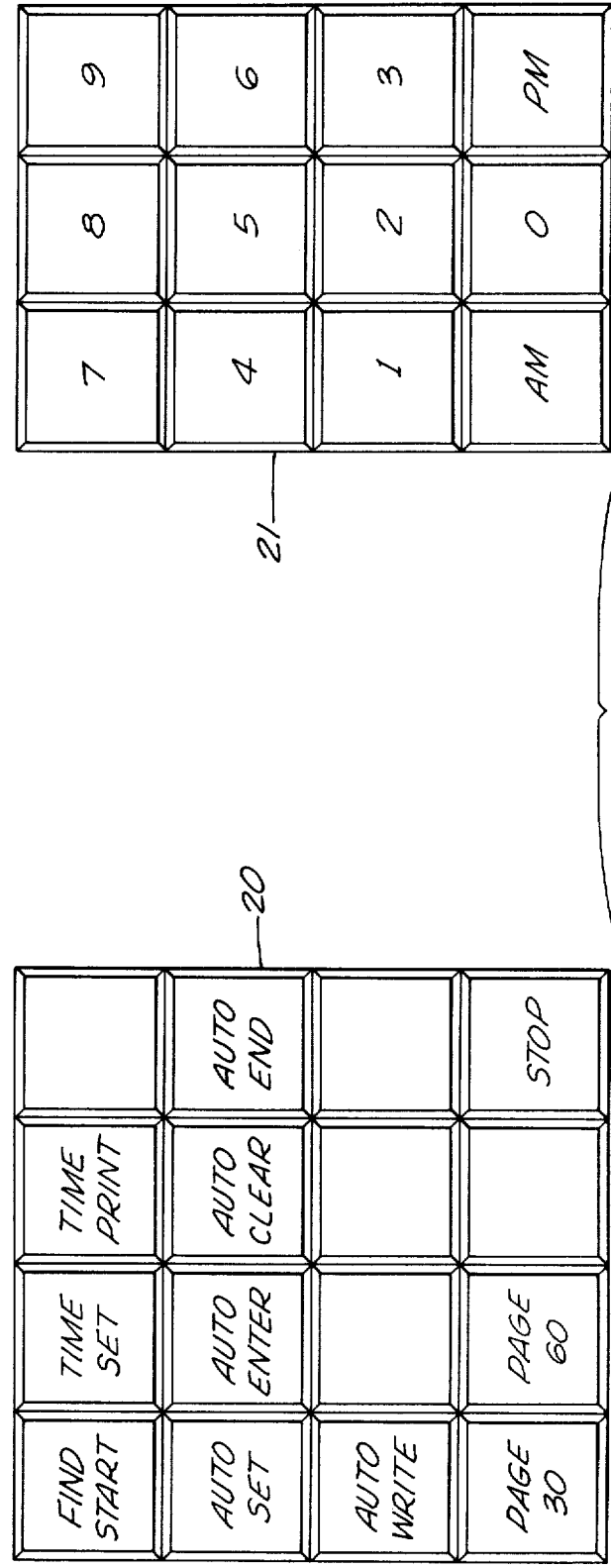
FIG. 3 is an enlarged plan view of the function keypad and alpha-numeric keypad from that preferred embodiment.

FIG. 3 shows the indicia on the function input keypad 20 and on the alpha-numeric input keypad 21. Keypad 20 permits selection of the various functions which the processor can perform. Keypad 21 permits selection of alpha-numeric data for display and transcription, and also permits selection of the frequency with which alpha-numeric data appears in the transcription.

Figure 4B:
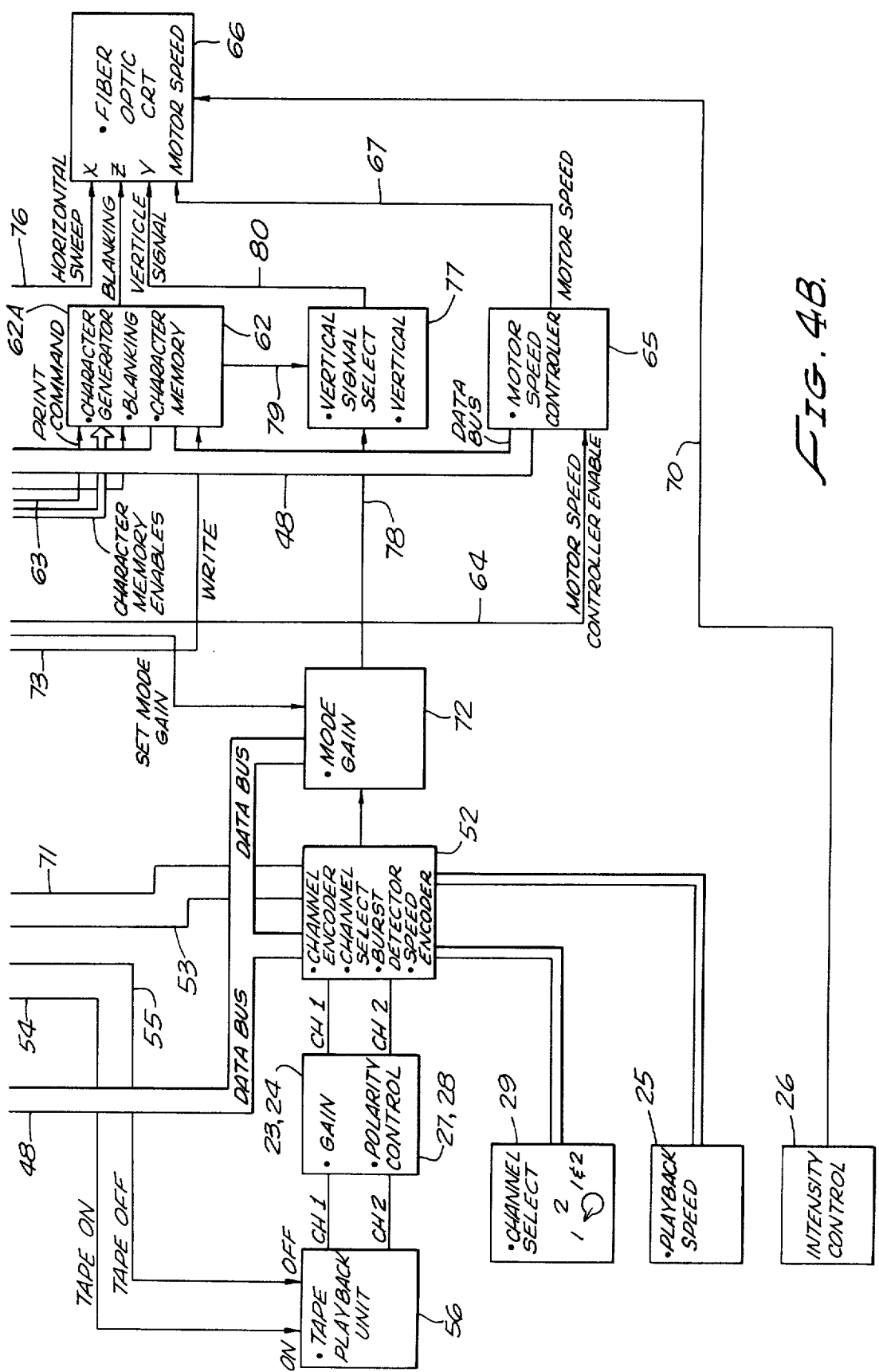

FIGS. 4A and 4B show, in function block diagram form, the components of the preferred embodiment, including microprocessor 46, keypads 20 and 21, and stored program means 47. Data bus 48 carries data to all components of the processor, including data originating in microprocessor 46 and data originating in the other components. Address bus 49 carries commands for data from microprocessor 46 to address decoder 50, which calls instruction data from program means 47 onto data bus 48.

Microprocessor 46 and program means 47 operate as follows. Every instruction in the program has an address. These addresses are organized in sequence. Inside microprocessor 46 is a counter which registers the address of the program instruction being executed. Microprocessor 46 passes the address of the instruction on address bus 49 to address decoder 50. Via command to program 47 on path 51, decoder 50 then enables only the instruction called for to appear on data bus 48. Microprocessor 46 receives the instruction from data bus 48, and executes that instruction. After executing the instruction, microprocessor 46 produces the address of the next instruction. Address decoder 46 produces the address of the next instruction. Address decoder 50 enables that instruction to come onto data bus 48, and the process repeats itself. Because each component of the processor has a unique address, microprocessor 46 can utilize common data bus 48 to control one, two or any combination of processor components without affecting any other component.

Processor functions are selected by activating the appropriate switches on face plate 3, function keypad 20 and alpha-numeric data keypad 21. The operation of the controls on face plate 3 is set forth above. After the gain, polarity, channel select, speed and intensity are appropriately activated at plate 3, the processor is ready for instructions from keypad 20. In particular, with the processor components reset, microprocessor 46 calls a data word from keypad 20 onto data bus 48 by putting the address of keypad 20 or keypad 21 into decoder 50, which enables the data word onto data bus 48 via key data enable path 48. Microprocessor 46 continues to call and examine such data words from function keypad 20 until a key thereon has been activated. Once that happens, microprocessor 46 retains the data word from the keyboard, and finds the corresponding sequence of instructions in program 47. Microprocessor 46 then executes that sequence of instructions to carry out the desired function.

In a common sequence of operations, the operator places a reel or cassette of tape-recorded ECG data on cassette player 5 or reel-to-reel player 13, rewinds the tape to the beginning, and presses the FIND START switch on keypad 20. This command asks the processor to find and detect a burst of energy entered on the tape to mark the beginning of, or some other point of interest in the recorded data. The FIND START command word passes to microprocessor 46 on data bus 48, which feed the address of the burst detector reset command to decoder 50 and then to burst detector 52 via path 71; then, the same word commands the tape playback unit to start. Decoder 50 then resets the burst detector by passing a signal to burst detector 52 on path 53. A signal from decoder 50 carried on path 54 starts tape playback unit 56. The tape advances until the burst detector finds and detects the burst, and relays that information to the microprocessor 46 on data bus 48. Upon detection of the burst, microprocessor 46 commands decoder 50 to turn off tape playback unit 56. This command passes from decoder 50 on path 55 to tape playback unit 56. This completes the FIND START function.

Normally, ECG and EEG data are recorded in real time. Because the tape-recorded data ordinarily does not include the time of recording, the operator must input the time that recording began. To do so, the operator activates the TIME SET key on keypad 20. Microprocessor 46 reads the word from this command on data bus 48, and calls for data from alpha-numeric keypad 21. Commonly, the operator inputs the time that the recording of physiological data began from alpha-numeric keypad 21. As the operator inputs the numeric data for the time that recording began, that data passes on data bus 48 to buffer memory 57 and to readout memory 58. Under instructions from microprocessor 46 conveyed to decoder 50 on address bus 49, decoder 50 enables storage of the alpha-numeric data by commands on paths 59 and 60 to memories 58 and 57, respectively. Once enough alpha-numeric data has been entered to indicate the time recording began, including the hour, minute and a.m. or p.m., the data is examined to determine whether it is a reasonable time (i.e., not an unreasonable time such as 31:75 a.m.). As the alpha-numeric data is input, that data is visibly displayed at display 45 (FIG. 2). If the input data is unreasonable, the processor rejects that data and indicates rejection at, say display 45. Thereupon, the microprocessor looks to function keypad 21 for its next instruction.

Typically, the operator next activates the TIME PRINT key switch. This command passes via data bus 48 to microprocessor 46, which calls for alpha-numeric data from keypad 21 to indicate the frequency with which the alpha-numeric data is to be displayed and transcribed on the photosensitive paper. When entered, that frequency interval passes via address bus 49, decoder 50, and readout memory enable path 69 to memory 58. Further, the interval appears visibly at display 44 (FIG. 2). The processor permits selection of frequency from a wide range. In the preferred embodiment, the range of choices is from none at all to once every 60 minutes.

With the FIND START, TIME SET and TIME PRINT functions completed, the processor is ready to convert the recorded data to electrical signals, display them as light signals, and transcribe the light signals onto photosensitive paper. To do so, the operator must then select the mode of display and transcription. In the preferred embodiment, those modes are called PAGE 30, PAGE 60 and AUTO WRITE. Activation of the PAGE 60 key on keypad 20 calls for transcription of 60 lines of data, each line including 60 seconds of data, on 10.5 inches of paper. Activation of the PAGE 30 mode calls for display of 60 lines of data on 10.5 inches of paper, each line including 30 seconds of data. These formats are arbitrary, and the processor can be set to print in a wide variety of modes.

Upon activation of the PAGE 60 key, microprocessor 46 activates timer hardware 60, which controls the intervals at which data sweeps across the face plate of the fiber-optic recorder 66. In PAGE 60 mode, reset of sweep signals occurs after 60 seconds of data are displayed on a line. Timer hardware 60 is enabled by a signal from decoder 50 fed via timer enable path 74.

Horizontal sweep generator 61 controls the movement of the fiber-optic recorder's electron beam across the face plate of recorder 66 in the horizontal plane. To enable horizontal sweep generator 61, a signal from decoder 50 passes thereto on sweep rate enable path 75. Generator 61 conveys a command to fiber-optic CRT 66 on path 76. A swingle sweep across the face plate of the recorder is directly related to a specific time interval, here 60 seconds of data. After 60 seconds of data are displayed, sweep generator 61 resets to display the next 60 seconds of data, on a new line. The process repeats until all the data, or those portions of the data selected by the operator are displayed and transcribed.

In effect, the processor keeps time by reference to the reset frequency. Each reset takes place after a fixed amount of time. In the PAGE 60 mode, that amount of time is 60 seconds of real time; in the PAGE 30 mode, 30 seconds. In the AUTO WRITE mode, described hereafter, reset occurs every 10 seconds of real time data. Microprocessor 46 monitors the number of resets, and converts them into real time equivalent on the alpha-numeric readout. Upon command from microprocessor 46, that real time is displayed and printed on the photosensitive paper.

Microprocessor 46 also controls the speed at which the photosensitive paper moves past the display (cathode ray tube, or CRT) of recorder 66. In PAGE 60 mode, one hour of ECG data can be transcribed onto about 11 inches of paper. Microprocessor 46 controls paper speed by passing a command on path 64 to motor speed controller 65, which in turn controls motor speed at the CRT by a signal on path 67.

Vertical signal select means 77 controls vertical movement of light signals on the face plate of fiber-optic recorder 66. To do so, select means 77 receives a mode gain signal from mode gain control 72 via path 78, or a character generating signal from character generator 62A via path 79. Vertical control commands pass from vertical control means 77 via path 80 to recorder 66. In the PAGE 60, PAGE 30 and AUTO WRITE modes, microprocessor 46 generates a command to set the mode gain means 72 via decoder 50 and data bus 48. A signal from decoder 50 via set mode gain path 73 enables mode gain means 72 to accept this command. This command controls vertical displacement of the physiological data signals on the face plate of recorder 66.

To display alpha-numeric data on the face plate of fiber-optic recorder 66, the vertical and horizontal sweeps must be coordinated to generate a raster, or two-dimensional sweep pattern. By modulating intensity of the recorder's electron beam in a timely fashion, a pattern of dots forming an alpha-numeric character generator appears on the face plate. Character generator 62 includes a memory 62A for storing alpha-numeric data to be displayed and printed. Microprocessor 46 simultaneously generates commands, through decoder 50, to store alpha-numeric characters for output and display at the correct time, to put alpha-numeric data onto data bus 48, and to enter alpha-numeric data into character memory 62A. After the desired alpha-numeric data are entered into memory 62A, character generator 62 waits for a print command. Microprocessor 46 generates this command by passing the appropriate address, via address bus 49, into address decoder 50, which enables print command line 63 to display the desired alpha-numeric data. When display is complete, character generator 62 stops and waits for the next print command.

In addition to its capacity to display and print at high speed all the physiological data from one, two or both channels of such tape as magnetic tape, the new processor can also automatically and rapidly display and transcribe selected portions of data. To this end, the operator selects the appropriate tape channel for transcription, such as channel 1, channel 2, or channels 1 and 2 simultaneously, selects the appropriate polarity, gain and speed of tape playback, and then activates the AUTO SET switch on keypad 20. Microprocessor 46 detects that signal on data bus 48 and calls for entry of the desired time periods of data. Entry is effected in the way described with reference to the TIME SET function. After entry of each desired time period for transcription, the operator then presses the AUTO ENTER key to store that time period in buffer memory 57. When the last of the desired time periods is entered, the operator presses the AUTO END key, and the processor is ready for operation in the AUTO WRITE mode.

Upon activation of the AUTO WRITE key, the tape playback unit starts and advances to the beginning of the first time period to be transcribed. The scanner waits until about three minutes before that beginning time, then turns on the fiber-optic recorder's CRT. Then, about 2.5 minutes later, the sweeps are activated, and the beginning time of the first period to be transcribed is printed. After that, the ECG information is displayed and transcribed. The sweeps move the electron beam at appropriately rapid rates to spread the data out horizontally on the display and on the photosensitive paper. Vertical gain is approximately doubled automatically from the gain used at PAGE 30 and PAGE 60 modes, in the presently preferred embodiment, by controlling the vertical gain means 72 through a command from microprocessor 46 carried on data bus 48. (Decoder 50 enables mode gain means 72 to receive data from data bus 48 by a signal carried via path 73.) This enlarges the ECG data vertically. After the scanner has printed five or six minutes of enlarged data, the fiber-optic CRT turns off until the tape moves to the next time period for transcription. The sequence continues until all the time periods entered in the buffer memory have been displayed and transcribed, whereupon the tape playback unit and the fiber-optic CRT turn off.

What is claimed is:

1. An apparatus for high-speed transcription of recorded physiological data onto light-sensitive media including tape-playback means for converting the data into electrical signals representative thereof, means for converting said electrical signals into light signals susceptible of high-speed transcription, means for generating a signal for selecting alpha-numeric data from storage means for transcription with said light signals, and means for generating signals to control said data-converting means, signals to control said electrical signal converting means, and signals for controlling the frequency at which said alpha-numeric data is transcribed onto said light-sensitive media.

2. The apparatus of claim 1 further comprising means for displaying the selected alpha-numeric data in visually perceptible form.

3. The apparatus of claim 1 further comprising means for testing the reasonableness of the selected alpha-numeric data.

4. An apparatus for high-speed transcription of recorded physiological data onto light-sensitive media including tape-playback means for converting the data into electrical signals representative thereof, means for converting said electrical signals at high speed into light signals susceptible of substantially complete high-speed transcription onto light-sensitive media, means for automatic enlargement and transcription at high speed of at least one selected time period of said recorded physiological data, and means for generating signals for controlling said tape-playback means, signals for controlling said electrical signal converting means, and signals for controlling said means for automatic enlargement and transcription at high speed of at least one selected time period of said recorded physiological data.

5. The apparatus of claim 4 wherein the automatic transcription is initiated in response to an input signal representing a selected time period of recorded information.

6. The apparatus of claims 4 or 5 wherein the recorded physiological data is recorded on magnetic tape having at least two channels of recorded physiological data thereon.

7. The apparatus of claims 1, 4 or 5 further comprising means for transcribing, in conjunction with said light signals, the actual time of recording said electrical signals.

8. The apparatus of claims 1, 4 or 5 further comprising means for controlling the size of the transcribed physiological data.

9. The apparatus of claims 1, 4 or 5 further comprising means for selecting the speed at which recorded physiological data is converted into electrical signals.

10. The apparatus of claims 1, 2, 4 or 5 wherein the transcribing means includes fiber-optic recorded means.

* * * * *